United States Patent [19]

Fleischle

[11] Plant 4,945

[45] Nov. 16, 1982

[54] VARIETY OF STREPTOCARPUS NAMED DOLLY

[75] Inventor: Gerhard Fleischle, Vaihingen, Fed. Rep. of Germany

[73] Assignee: Oglevee Associates, Inc., Connellsville, Pa.

[21] Appl. No.: 204,202

[22] Filed: Nov. 5, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus plant is characterized by its plum-purple flower and its miniature form suited for small pots.

1 Drawing Figure

BACKGROUND OF THE NEW PLANT

The present invention comprises a new and distinct cultivar *Streptocarpus* × *hybridus* known by the varietal name Dolly. The new cultivar is a mutation achieved through irradiation of Marna, formerly named Neptune Blue (U.S. Plant Pat. No. 4,524).

While the new cultivar is most similar to Marna, Dolly is a miniature form suited for small pots. The color is more closely associated with that of Nicky (U.S. patent application). However, the foliage is slightly broader than Nicky.

The new cultivar was discovered in 1979 in Vaihingen, Federal Republic of Germany; was first asexually reproduced by cuttings in Vaihingen, Federal Republic of Germany; and has been asexually reproduced by cuttings at Oglevee Floral Company in Connellsville, Pa. It has been found to retain its distinctive characteristics through successive propagations.

DESCRIPTION OF THE DRAWING

The accompanying drawing illustrates the new cultivar.

DESCRIPTION OF THE NEW PLANT

The following detailed description sets forth the characteristics of the new cultivar. The data which defines these characteristics were collected from asexual reproductions carried out by Gerhard Fleischle in Vaihingen, Federal Republic of Germany. The color references are primarily to the R.H.S. color chart of the Royal Horticultural Society of London unless otherwise referenced.

The color references were collected from asexual reproductions carried out by Oglevee Floral Company in Connellsville, Pa.

Botanical classification: Gesneriaceae (Family): *Streptocarpus* × *hybridus* (Genus × Species).

Flower:

- *Fully expanded.*—Five and one-half centimeters.
- *Borne.*—In clusters of one to six flowers per stalk above foliage. Flower stalks arise from mid-rib of each leaf.

- *Stems.*—Single, long and pubesscent.
- *Form.*—Funnel formed in an umbel.

Color:

- *Front of petals.*—Fan 2 Violet Blue Group 84-B.
- *Throat.*—Fan 1 Yellow-Green Group 1-B with a plurality of stripes. Fan 2 Violet Blue Group 89-A extending in center of petals.
- *Base of petals.*—Fan 2 Violet-Blue Group 88-A.
- *Reverse of petals.*—Fan 2 Violet Group 83-B.
- *Tonality from a distance.*—Exotica 55 Moorish Blue.
- *Discoloration.*—Insignificant.

Petals:

- *Texture.*—Velvet.
- *Appearance.*—Individually lobed and smooth margin.
- *Arrangement.*—Regularly united into an elliptical form.
- *Fragrance.*—None.

Reproductive organs:

- *Anthers.*—Two per flower and interconnected.
- *Pollen.*—Generally nonfertile.

Plant:

- *Form.*—Leaves rosulate from a crown at the soil line.
- *Growth.*—A spreading, free flowing habit with leaf bases being attenuate.
- *Height from soil line.*—10 to 15 centimeters.
- *Spread.*—30 to 35 centimeters.

Foliage:

- *Size.*—Approximately 18 centimeters in length and 6 to 10 centimeters in width at the widest point.
- *Shape.*—Oblanceolate.
- *Top side.*—Fan 3 Green Group 137-A.
- *Underside.*—Fan 3 Yellow-Green Group 146-D.
- *Rib and vein color.*—Fan 3 Green Group 139-D.
- *Ribs and veins.*—Pinnate.
- *Margin.*—Crenate serrations.
- *Stipules.*—None.

I claim:

1. A new and distinct variety of Streptocarpus substantially as herein shown and described.

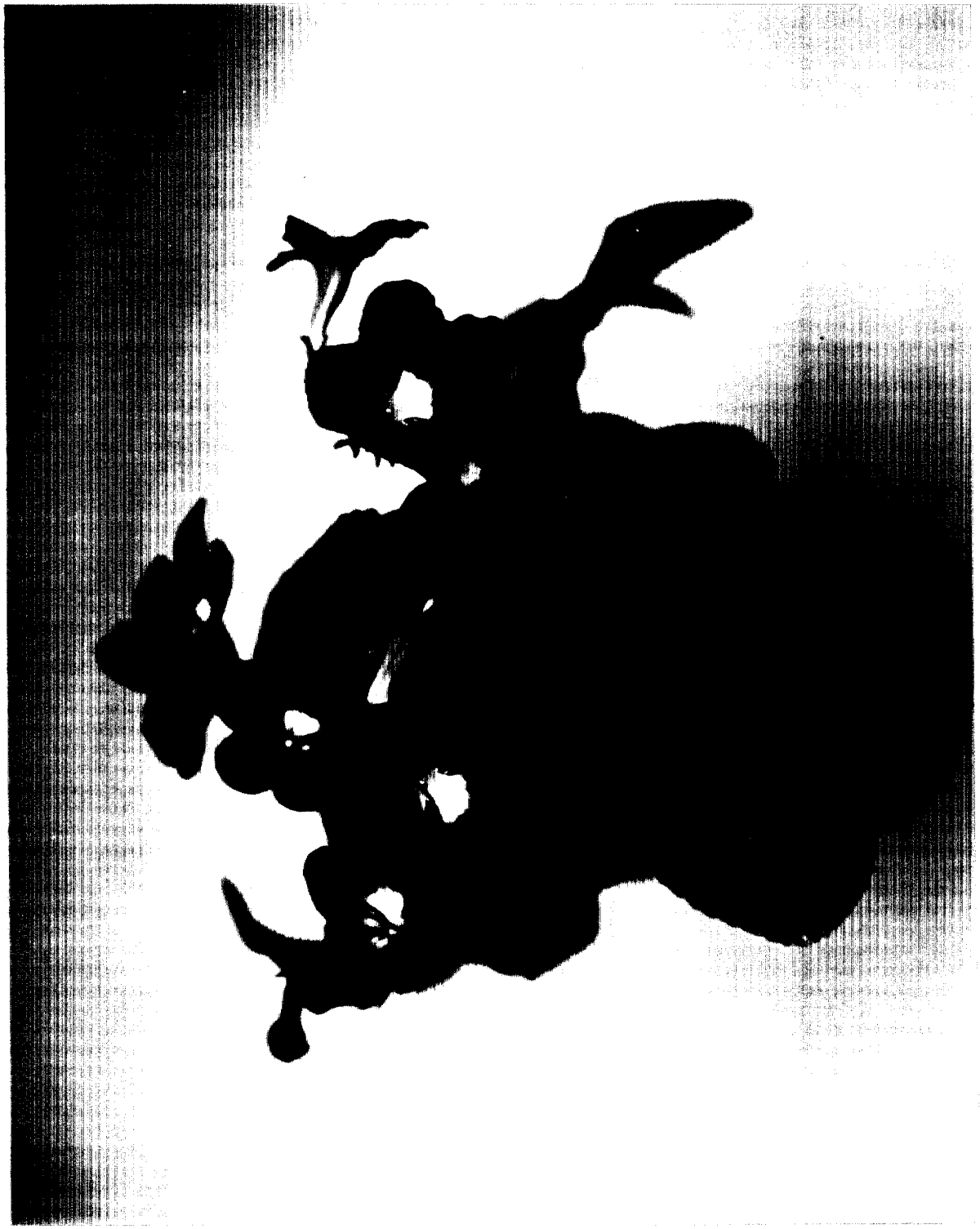

* * * * *